United States Patent [19]

Annis

[11] 4,228,357
[45] Oct. 14, 1980

[54] DETECTOR ON WHEEL SYSTEM (FLYING SPOT)

[75] Inventor: Martin Annis, Newtonville, Mass.

[73] Assignee: American Science and Engineering, Inc., Cambridge, Mass.

[21] Appl. No.: 966,227

[22] Filed: Dec. 4, 1978

[51] Int. Cl.³ ............... G01N 21/34; G01N 23/04
[52] U.S. Cl. .................... 250/445 T; 250/360; 250/363 S; 250/505
[58] Field of Search .......... 250/445 T, 363 S, 512, 250/505, 360

[56] References Cited

U.S. PATENT DOCUMENTS 3,780,291  12/1973  Stein et al. ........................ 250/363
3,970,853   7/1976  Kuhl et al. ..................... 250/445 T Primary Examiner—Alfred E. Smith
Assistant Examiner—Thomas P. O'Hare
Attorney, Agent, or Firm—Pollock, Vande Sande & Priddy

[57] ABSTRACT

An arc-shaped X-ray beam penetrates an arcual cross-sectional area of a body and the attentuated transmitted beam irradiates a portion of a circular array of detectors on a rotating disc. The detectors operate to generate signals proportional to the intensity of the incident transmitted radiation. The beam and detectors are moved along the axis of the body during rotation of the disc to irradiate adjacent cross-sectional areas of the body. A computer operated CRT receives the detector signals and displays an image of the radiation attenuation characteristics of the scanned arcual areas.

35 Claims, 7 Drawing Figures

FIG. 3
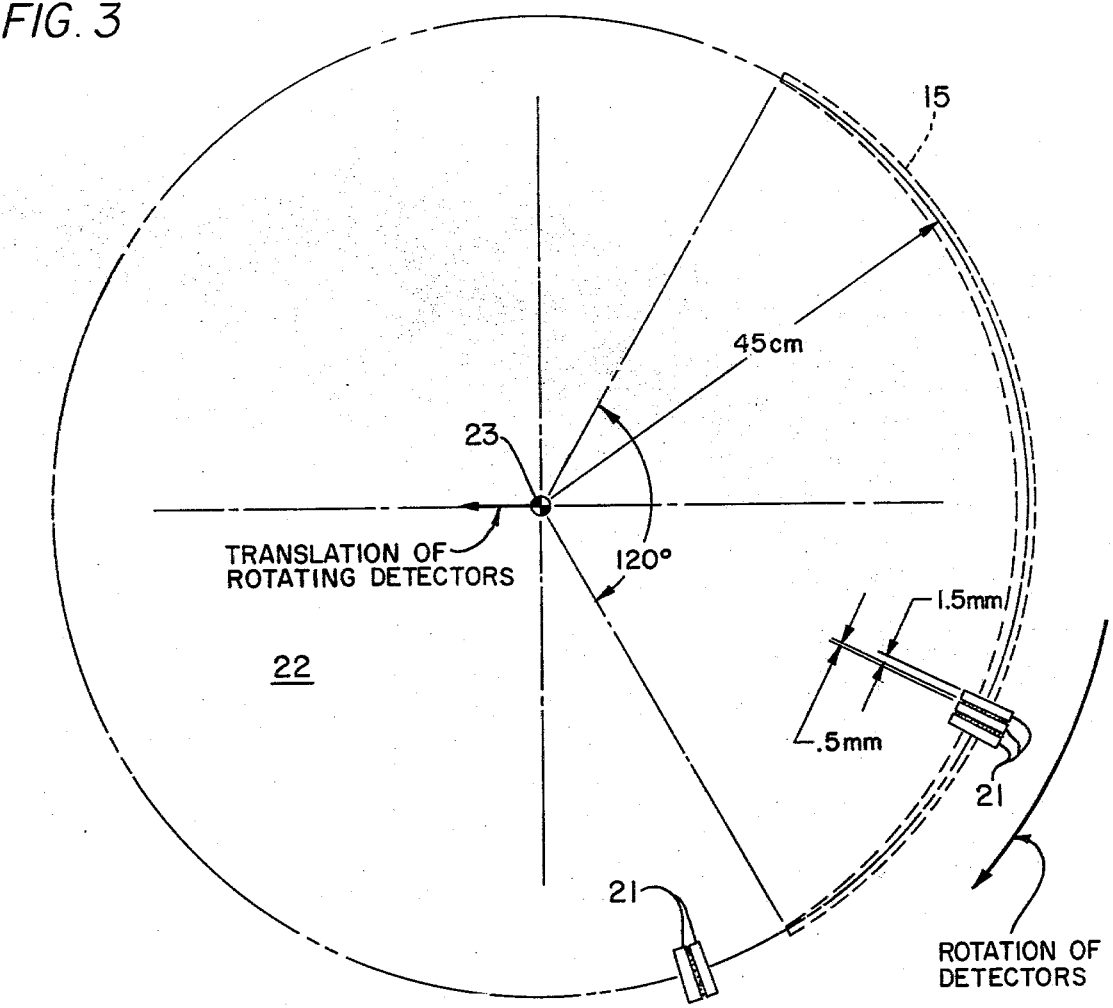
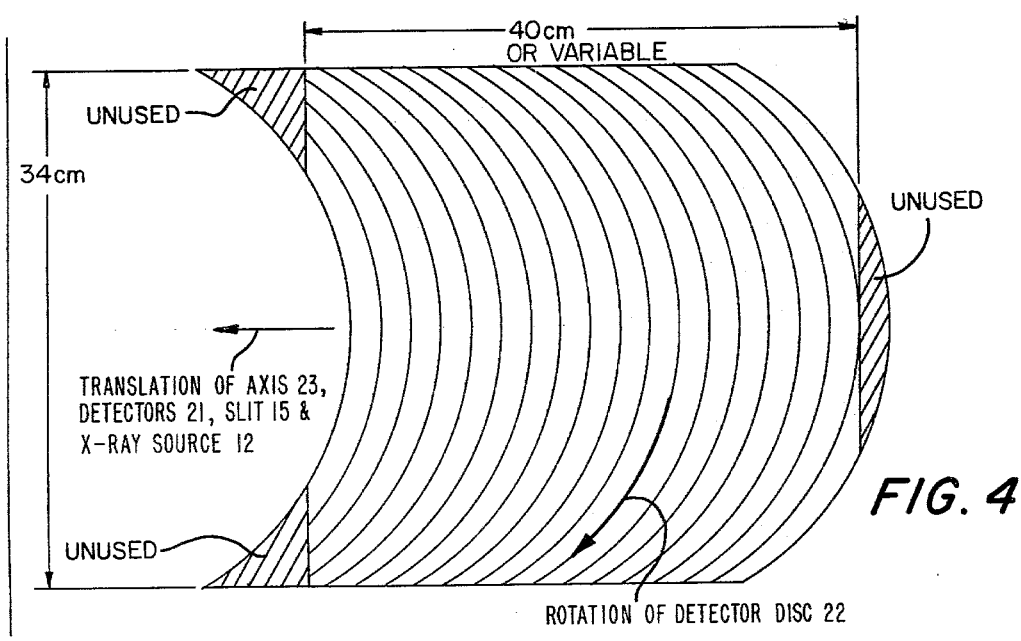
FIG. 4

DETECTOR ON WHEEL SYSTEM (FLYING SPOT)

BACKGROUND OF THE INVENTION

The present invention relates in general to radiant energy imaging and more particularly concerns novel apparatus and techniques for producing a two-dimensional image of the X-ray response of a scanned region of a patient. The invention is characterized by high contrast, low radiation scattering, and other features desirable in a diagnostic imaging system.

This invention is an improvement of the commercially available American Science and Engineering MICRO-DOSE ® system disclosed in U.S. Pat. No. 3,780,291, which has a moving pencil beam of X-rays that repeatedly scans the entire length of one detector as the target body translates past the scanning beam and detector assembly.

It is an important object of this invention to provide an improved radiant energy imaging system for diagnostic purposes.

It is a further object of the invention to provide such a system with relatively high efficiency and relatively low radiation scattering.

It is another object of the invention to achieve one or more of the preceding objects with a system that produces high-quality, high-contrast images.

A further object of the invention is to provide signals compatible with a digital computer display so that each pixel of the image may be conveniently exhibited with enhanced contrast by the physician or other user.

It is another object of the invention to achieve one or more of the preceding objects with a system in which sensitivity variations between detectors will not materially affect the quality of the image.

SUMMARY OF THE INVENTION

According to the invention, an X-ray opaque housing surrounds a source of a cone-shaped beam of X-rays. A stationary arcual slit in the front of the housing typically subtends an angle of $2\pi/3$ radians and collimates the cone-shaped beam into an arc-shaped fan beam that passes through an arcual crosssectional area of a body and irradiates a circular array of detectors mounted on the periphery of a rotating disc. Each detector scans the entire fan beam in one rotation of the disc and during or after each rotation of the disc the fan beam is moved about one millimeter or less along the axis of the body to irradiate an adjacent cross-sectional area of the body. A computer receives the signal data of the detectors and combines the data to produce a two-dimensional image of the radiation attenuation characteristics of the scanned areas of the body.

Numerous other features, objects and advantages of the invention will become apparent from the following specification when read in connection with the accompanying drawings in which like reference numerals designate identical apparatus.

BRIEF DESCRIPTION OF THE DRAWINGS

FIG. 3 is a diagrammatic representation of the rotating detector array according to the invention;

FIG. 4 is a graphical representation of the geometry of the measurements recorded by one detector during a complete translation of the source and detector assembly shown in FIG. 1.

FIG. 6b illustrates a front view of the apparatus of FIG. 6a.

DETAILED DESCRIPTION OF PREFERRED EMBODIMENTS

Figure 1:
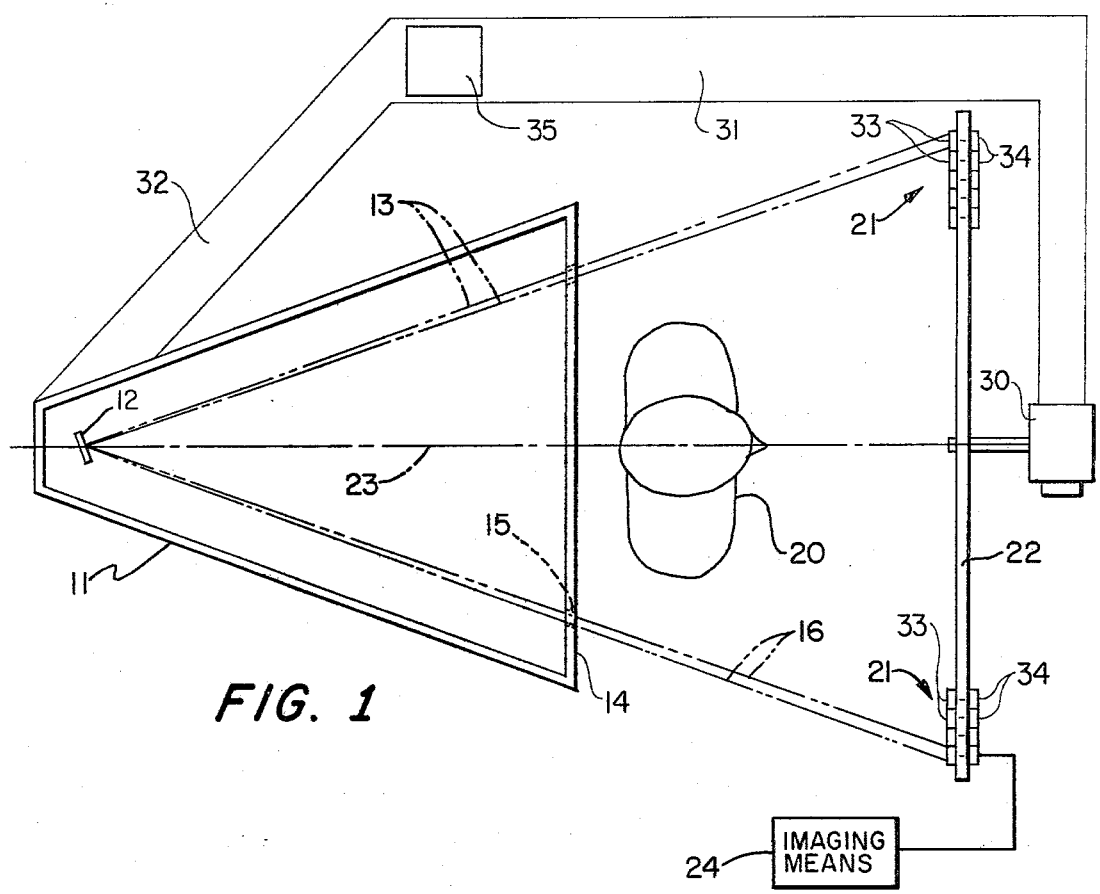
FIG. 1 is a combined block-diagrammatic representation of the X-ray source and detector array configuration according to the invention.

With reference now to the drawings and more particularly to FIG. 1 thereof, there is shown a combined block-diagrammatic representation of a high energy radiation source, for example an X-ray source 12, and a detector configuration according to the invention. The X-ray source 12 emits a cone-shaped beam of radiation 13 and is surrounded by an X-ray opaque housing 11. The beam 13 strikes an X-ray opaque plate 14 that may be positioned 50 centimeters from the source 12. An arcual slit 15 in the plate 14 collimates the incident X-rays into an arc-shaped fan beam 16.

The collimated fan beam 16 is directed at a body 20 that is positioned between the plate 14 and a circular array of detectors 21. The radiation intensity of the incident fan beam is sufficient to allow the beam to pass through an arcual cross-sectional slice of the body 20. However, it should be appreciated that the radiation intensity of the beam is attenuated as the beam passes through the body 20 and the relative amount of attenuation of the beam provides information as to the structure of the internal slice of the body under examination.

The intensity of the attenuated transmitted radiation of the fan beam 16 is measured by the circular array of detectors 21. The detectors 21 are mounted on the periphery of a circular disc 22 that may be 40 centimeters from the plate 14. A motor 30 rotates the disc about an axis 23 so that each detector of the circular array may independently scan across the transmitted attenuated radiation of the fan beam 16. Therefore, after one rotation of the disc 22, each detector has scanned across the transmitted beam and has thereby provided an independent measurement of the radiation intensity of the beam and the associated attenuation properties of a cross-sectional arcual slice of the body 20 under examination.

During each rotation of the disc 22, the X-ray housing 11 and the disc 22 are translated in a manner known to the art a fixed distance along the axis of the body 20 in a direction perpendicular to the axis of rotation 23. For example, the rotating motor 30 can be adapted to operate a hydraulic pressure system to move an upright post 35 in an axial direction. The axial movement of the post 35 can then be translated to rigid arms 31 and 32, respectively coupled to the disc 22 and the X-ray housing 11, to move the housing 11 and the disc 22.

The new adjacent axial position of the fan beam 16 and the detectors 21 causes an adjacent arcual cross-section of the body 20 to be irradiated by the beam and the corresponding rotation of the disc 22 causes each detector to scan the beam to measure the beam attenuation through the new crossectional slice of the body 20.

In a similar manner, the apparatus of the invention moves along the axis of the body to measure the intensity of radiation that is transmitted through succeeding cross-sectional slices of the body 20. Of course, it should be appreciated that the speed along the axis of the body is determined by the speed of the rotation of the disc 22, since the disc must rotate at least once to measure the transmitted radiation intensity associated with a particular cross-sectional area of the body 20.

Each of the detectors 21 is adapted to generate an electrical signal that is proportional to the intensity of incident radiation. Such detectors are known to the art and may include scintillator crystals 33, for example of sodium iodide, cesium iodide or bismuth germanate, to generate light energy in response to the incident fan beam radiation. The crystals 33 are in operative association with elements 34, for example photomultipliers, that translate the light energy to corresponding electrical signals. Alternatively, the elements 34 could include known solid state devices that generate corresponding electrical signals in response to incident radiation.

The electrical signals that are generated by the detectors are applied to an imaging means 24 that is adapted to store the signals and generate a visual representation of the attenuation characteristics of the irradiated arcual crosssections of the body 20.

Although the specific means for generating the visual display of the attenuation characteristics of the cross-sectional areas of the body 20 is not the subject of this invention, it should be understood that the video signals corresponding to the measured, transmitted radiation intensity will not produce an undistorted image if they are both stored and read in any standard rectangular fashion. Therefore, in order to produce a relatively undistorted image, either the storage addressing (data placement location) or readout addressing of the image storage medium could be arcual. Alternatively, the electron scanning beam of a CRT display device could be deflected in an arcual manner.

Figure 2:
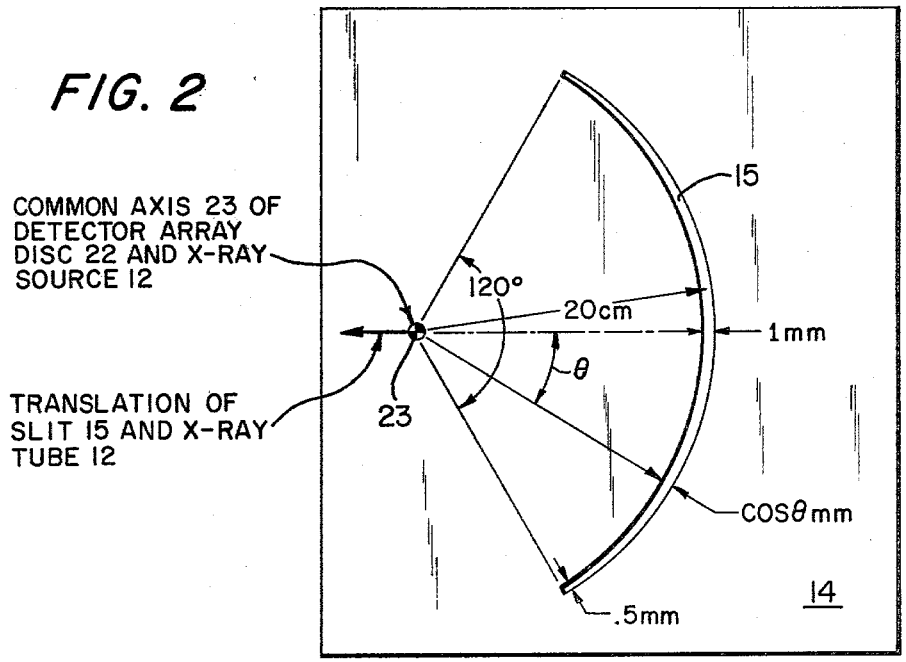
FIG. 2 is a diagrammatic representation of the arcual slit in the X-ray source housing according to the invention.

It should be appreciated that in all of the above arcual display modes, the arcual displacement from a straight line is in a direction along the translation axis (axis shown in FIGS. 2, 3 and 4). For example, for arcual storage addressing, if the image is stored in an Analog Video Storage Unit using a lithocon tube for storing a matrix of electrical charges having element values representing image pixel intensities, the high frequency horizontal ramp voltage for deflecting the electron beam in the lithocon tube would remain the same. However, the standard low frequency ramp, with an added arcual voltage having a frequency equal to the horizontal frequency, would be applied to the vertical deflection plates. The readout would then utilize both standard deflection ramp voltages.

It should be understood that delayed arcual storage addressing could be used to display the image. In such a display mode, the video data could be digitized and stored in a digital memory and a computer could be used to reconstruct the stored image in an arcual manner for display on a CRT.

Alternatively, an arcual readout scheme could be employed to read digitized image data from the memory of a computer by linear horizontal addressing in combination with arcual varying vertical addressing.

For the above examples of arcual storage and readout, the display may be produced on the CRT of a video monitor in a conventional manner, for example, as disclosed in U.S. Pat. No. 3,780,291 for a MICRO-DOSE® beam scanning system. However, if arcual scanning of a CRT is used instead of arcual storage or readout, then the deflection of the electron scanning beam of the CRT is modified in the same manner as described above for the electron scanning beam of a lithocon tube.

FIG. 2 illustrates the structure of the collimation plate 14 in accordance with a preferred embodiment of the invention. Although the invention is not limited to the particular indicated dimensions of the features of the collimation plate 14, it has been determined that such dimensions may be used in the operation of the invention. As shown in FIG. 2, the arcual slit 15 in the collimation plate 14 subtends an angle of substantially $2\pi/3$ radians and, more particularly, the slit covers an arc of 120° of a circle with a radius of 20 centimeters.

The width of the slit 15 ranges from one millimeter at its center to 0.5 millimeter at either end, with the variation in width from the center to the ends defined by the $\cos \theta$, where $\theta$ is the angular distance from the 1 mm center point of the slit 15. The slit is tapered in this fashion to provide a substantially uniform X-ray exposure at each point of the target body 20.

FIG. 3 illustrates the structure of the rotating disc 22 and the associated detectors 21 in accordance with a preferred embodiment of the invention. Approximately 1400 detectors, 1.5 millimeters in width and arranged 2 millimeters apart center-to-center, are disposed on the periphery of the disc 22 of radius 45 centimeters. The disc is adapted to rotate at approximately 2400 rpm so that each detector will scan across the fan beam in approximately 25 milliseconds, or one revolution of the disc.

It should be appreciated that in any instant of time the collimated arc-shaped fan beam 16 will be directed to $\frac{1}{3}$ of the detectors 21, since the collimated fan beam subtends an angle of substantially 120°.

While the disc 22 is rotating, the collimated fan beam 16 may be either periodically incremented or continuously translated a fixed distance along the axis of the body 20 in a direction perpendicular to the axis of rotation 23. For better spatial resolution, incrementation is required. However, for a cheaper engineering design, continuous translation should be used.

If a mechanical incrementing movement is used, the incrementing movement may be applied to the complete housing 11 and the disc 22. However, it is more practical to increment only the plate 14. It should be understood that providing such an incremental movement over time periods measured in milliseconds causes large G forces to be applied to the moving apparatus. For example, if the plate 14 is incremented a distance of 1 mm within 1 millisecond, the associated acceleration or deceleration would be more than 400 G If the time period is increased to 8 ms, the resulting G forces is more than 6 G.

The operation of a system employing an incrementally moving plate 14 may be better understood by reference to the following example in which it is assumed that the disc 22 rotates at 2400 rpm (1 rev/25 ms), the incrementation takes 8 ms, and the housing 11 and disc 22 translate smoothly at a speed of $v=0.75$ mm/rev.

In such a system, the plate 14 would translate smoothly in a direction opposite the direction of the housing 11 and disc 22 at a velocity of $-V$ for the time (25 ms) that it takes the disc 22 to complete one revolution and thereby record the scanned data.

Thereafter, in a time of 8 ms, the plate 14 would be moved an incremental distance of 1 mm in the direction of the moving housing 11 and the disc 22. During the 8 ms period of incremental movement, data would not be recorded and the disc 22 would rotate approximately ⅓ rev.

After the 8 ms incremental movement interval, the plate 14 would again be smoothly translated at a velocity of −V and the next cycle of data aquisition would begin. Thus, a new data aquisition cycle would begin after every 1⅓ revolutions of the disc 22 and 25 ms of each 33⅓ ms cycle would be used to acquire data.

Figure 6A:
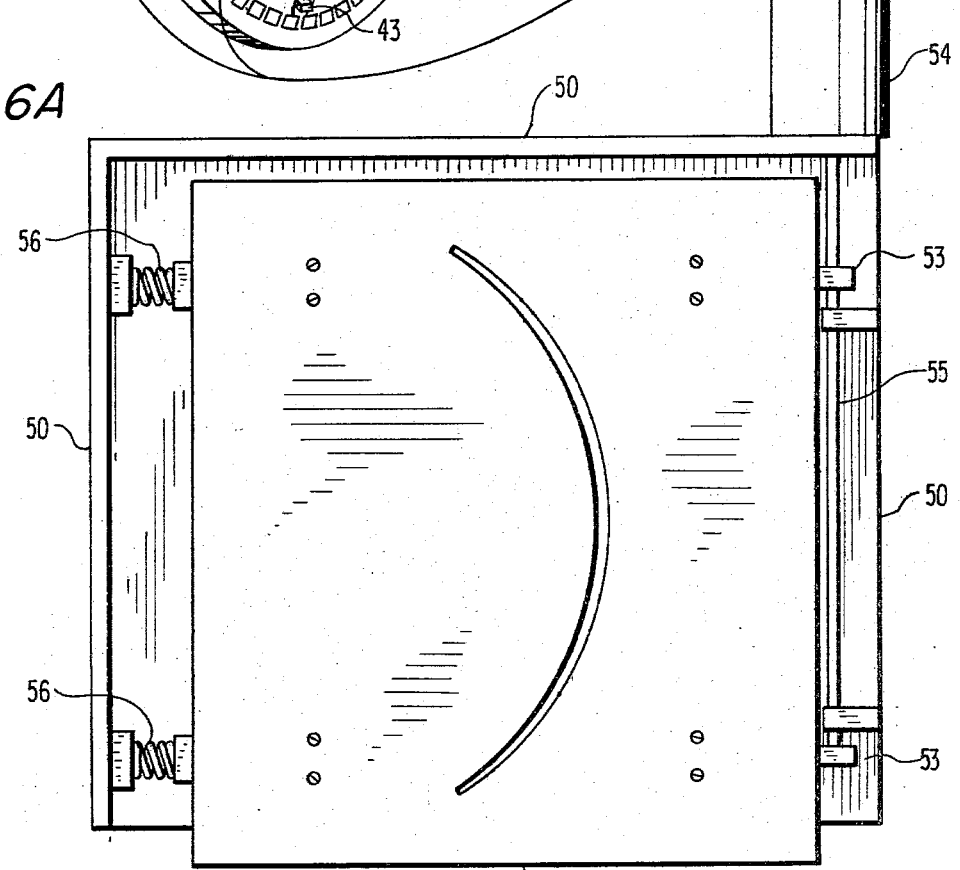
FIG. 6a illustrates a top view of an apparatus for mechanically incrementing a translating plate.
Figure 6B:
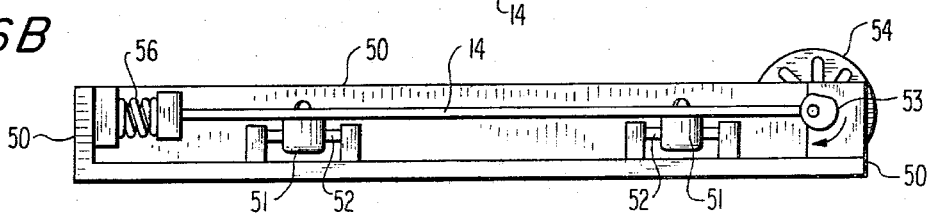

An apparatus for mechanically incrementing a translating plate 14 relative to the housing 11 and disc 22 in the manner described above is shown in FIGS. 6A and 6B. The plate 14 is translated relative to its mounting structure 50, which is in turn rigidly mounted to the housing 11. The plate 14 is coupled to the structure 50 by four ball-bushings 51 and their respective shafts 52. The proper translation force on the plate 14 is provided by cams 53 that are turned by a shaft 55 of a motor 54. The plate 14 is kept in contact with the cams 53 by an opposing force that is applied by springs 56. If the disc 22 is rotating at 2400 rpm and the mechanical incrementation occurs each 4/3 revolution of the disc 22, the motor 54 must rotate at a speed of 1800 rpm (3/4·2400).

It should be appreciated that in the above incremental movement system, some rotation time of the disc 22 is sacrificed in order to allow the incremented translation of the plate 14 to occur without causing blurring in the direction of translation. In such a system, the radiation exposure efficiency is reduced to 75% of that obtained by continuous translation if the radiation is not blocked during the incrementation phase. However, synchronized control of the radiation during the incrementation phase may be accomplished, for example, by using a mechanical shutter or a pulsed X-ray tube.

Incrementation can also be performed by a mechanically continuous but optically incremental motion, such as would be applied in a spiral scanning geometry. In such a scheme the detectors would not all be positioned at a radial distance of 45 cm, as shown in FIG. 3, but would be placed at a radial distance r defined by the expression:

$$r = (450 \text{ mm}) - (1 \text{ mm})(\theta/2\pi)$$

where $0 \leq \theta \leq 2\pi$.

Such a scheme would have the disadvantage that the radial length of the sensitive region of a detector would determine the spatial resolution (e.g., 1 mm size), since the arcual slit 15 in the plate 14 would have to be widened to completely irradiate each of the detectors. Also, it should be appreciated that the widened slit would decrease the radiation exposure efficiency of the apparatus. In addition, such a system would lose the effect of tapering the slit 15 to maintain a constant X-ray exposure. It should be understood that if such a continuous translation method is used, the amount of spatial blurring in the direction of translation can be reduced by reducing the amount of translation during each revolution of the disc 22.

FIG. 4 illustrates a graphical representation of the 400 beam scans that are made by one scanning detector over an axial distance of 40 cm and over a time period of 10 seconds. Of course, in accordance with the operation of the invention, during the above 10 second period the detectors made 560,000 total beam measurements, with successive measurements of a particular detector being separated by the 1399 measurements of the other detectors. As explained previously, the imaging means 24 combines the measurements of all of the detectors to produce a visual image with one millimeter resolution upon a television picture tube.

Due to the nature of the present invention, in which the detectors 21 continually rotate on the disc 22 while they are functioning, special electronic techniques are required to communicate the data from the detectors to the stationary system which displays the generated image. However, no special electrical techniques are required to supply power to the rotating disc 22. Standard methods such as slip rings 40 shown in FIG. 5 may be used to couple AC power to power supplies rotating on the disc 22. Alternatively, the same method may be employed to couple DC power from stationary power supplies to the disc 22. In such a DC power mode, noise suppression filters could be added to the disc.

Figure 5:
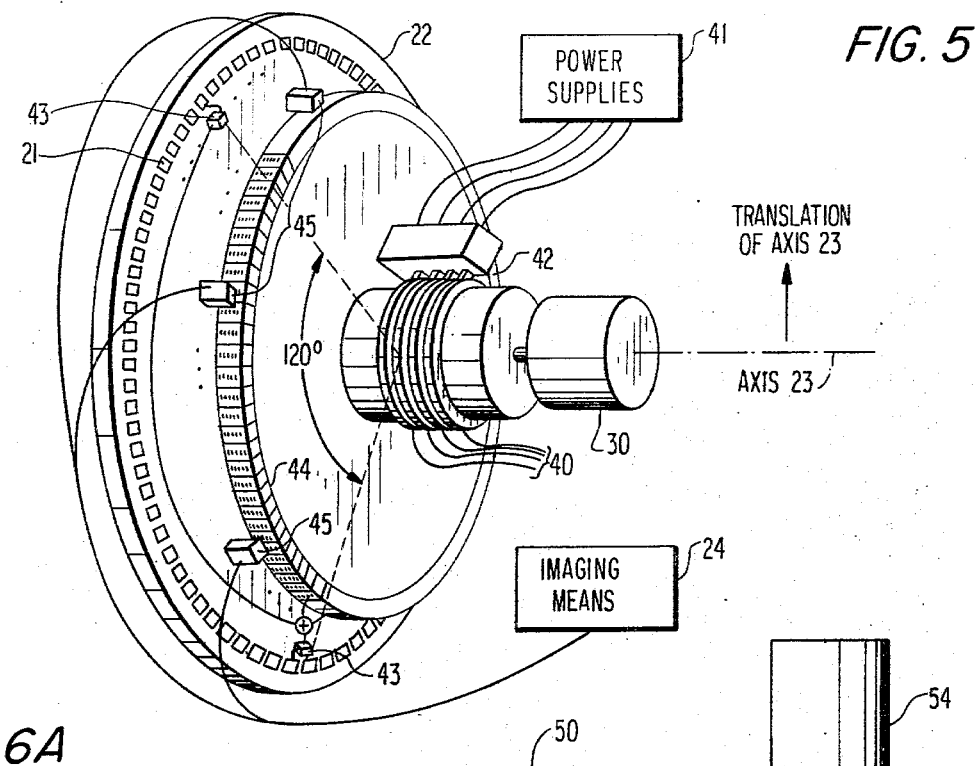
FIG. 5 is a diagrammatic representation of the method of supplying electrical power to the rotating detector array shown in FIG. 3 and of taking data from the rotating array.

FIG. 5 illustrates an embodiment of the invention in which DC voltages from several power supplies 41 are coupled to the disc 22 through a standard brush housing 42 and slip rings 40. Although the slip rings 40 could be used to transfer detector data from the disc 22, such a use is not desirable due to the large number of rings required and due to the noise generated at the brush/ring contacts.

The transfer of data could also be accomplished by using either an acoustical, radio frequency, or microwave transmitter/receiver system, however, the preferred embodiment of FIG. 5 uses optical transducers. More particularly, the signal from each of the detectors 21 is passed to a receiving circuit 43 including a preamp and a signal processing device such as an A/D converter, and the resulting signal is applied to an optical emitter 44, for example a series of LED's, to energize the LED's in a pattern corresponding to the applied signal. As the optical emitters are rotated, the corresponding optical signals are received by stationary optical receivers 45, for example photodetectors, that are positioned about the periphery of the ring of emitters 44. Each of the receivers 45 generates an electrical signal corresponding to the optical signal of its facing emitter and applies the electrical signal to the imaging device 24. Of course, the medium between the emitters 44 and receivers 45 is isolated from ambient light.

Commercially manufactured transducers are available wherein the emitters are octal sets of LED's and the associated receivers are spatially matched sets of phototransistors for coupling 8 bits of digital data.

It should be understood that the detectors 21, associated circuits 43, and optical transducers 44 and 45 are positioned in circular arrays about the axis of rotation of the disc 22. For example, if 1401 detectors are used, then 1401 preamps and associated A/D converters may be required. However, since only ⅓ of all of the detectors 21 are irradiated at any instant in time, only 1401/3 = 467 optical emitters are required. The number of associated electronic circuits 43 that are used will depend upon the function to be served by the circuits.

In order to operate with the above lower number of emitters, the signal from each detector 21 may be combined with two other associated detectors, for example by an adder, if proper threshold circuits are used. The output of the adder can then be applied to its associated emitter. It should be appreciated that the detector members of each detector triplet should be spaced 120° from one another in order to ensue that only one detector will activate the shared adder at an instant in time.

Regardless of the method of data transfer from the disc 22, the signal-to-noise ratio will not deteriorate if the transfer is done digitally, provided that the induced noise has an amplitude that is far less than the Boolean signal level. This criterion is easily satisfied if the optical transducers are used.

It should be understood that although the dimensions and other parameters of a preferred embodiment of the invention have been particularly described, the invention is not limited to the use of these particular dimensions and parameters. For example, the arcual slit 15 could be adapted to subtend an arc of less than or greater than $2\pi3$ radians without departing from the spirit of the invention.

In addition, the disc 22 could be rotated at any speed compatible with the response time of the detectors and the restraints imposed by the natural movement of the body under examination.

Furthermore, the total axial scanning distance could be changed or the 1 mm incremental scanning distance could be altered without substantially affecting the operation of the invention.

Also, the focal spot of the X-ray tube need not be on the same axis of the rotating detector wheel, which is the axis 23. Referring to FIG. 2, the focal spot could be displaced to the right of the axis 23, preferably by a distance not greater than the radius of the slit. Both the array of detectors and the slit would remain arc-shaped.

Moreover, although the small size of the detectors is an important feature of the apparatus of the invention, the actual dimensions and number of the detectors could be modified somewhat without substantially affecting the operation of the invention.

Also, although the operation of the invention is described with respect to an X-ray source of radiation, it should be understood that other types of high energy radiation could be used, for example, gamma rays.

The invention is characterized by a number of desirable features including the rejection of scattered radiation in the ratio of the area of the slit 15 to the area of the visual image. This ratio is about $2\pi R\delta/3\pi R^2$, or approximately $\delta/R$, where $\delta$ is the width of the slit 15 and R is the radius of the circle of the slit 15. In the described embodiment, the fraction $\delta/R$ is approximately 1/200. Thus, the apparatus of the invention produces only 0.5% of the scattered radiation of a conventional uncorrected radiograph. Furthermore, it is only the fluctuations in this 0.5% pickup of scattered radiation that creates noise, which is not true for conventional radiography.

Another feature is that each detector 21 may be extremely small and relatively low in cost, thereby facilitating the manufacture of the detectors.

A further advantage is that each detector produces a complete image, so that a variation in sensitivity between the detectors 21 or a sensitivity variation in a single detector 21 in a time longer than 25 milliseconds has no discernible effect on the quality of the final image. In prior art systems that employ single detectors to produce various portions of an image, variations in detector sensitivity cause apparent variations in measured beam intensity that do not correspond to the actual values of beam intensity and, therefore, artifacts in the displayed image may result.

Still another feature is that all of the detected X-rays may be used to improve the perceived contrast since each detector 21 produces a complete image. It has been determined that the minimum perceptible contrast between adjacent 1 millimeter resolution elements will be 1%, or about a factor of 5 better than conventional systems.

A further feature is that the apparatus of the invention may be used to produce a digital electronic image that can be displayed at a variety of levels by expanding the contrast at each level. The quality of the image would be limited only by the number of X-rays used per resolution element.

The present invention, with an entry exposure of about 80 mR, is about 200 times more efficient than the prior art MICRO-DOSE ® system that employed about 0.4 mR. The exit exposure for the apparatus of the invention is about 1 mR, or $\frac{1}{4}\times 10^6$ X-ray photons per millimeter resolution element. The minimum perceptible contrast is about 1% (using a 5 sigma criterion).

There has been described a novel radiant energy imaging system characterized by improved contrast, lower radiation scattering and greater efficiency than prior art scanning systems. It is evident that those skilled in the art may now make numerous uses and modifications of and departures from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A radiant energy imaging apparatus for displaying the characteristic radiation absorption of cross-sectional areas of an irradiated body, comprising:
   source means for generating penetrating radiation;
   collimating means for interrupting said radiation to pass an arc-shaped fan beam of radiation and to direct said fan beam to pass through a corresponding arc-shaped cross section of said irradiated body;
   a plurality of detectors arranged in an arc-shaped curve for receiving the unattenuated radiation transmitted through said arc-shaped cross section of the body and generating electrical signals corresponding to the intensity of the unattenuated radiation;
   means for rotating said detectors to scan each of said detectors at least once across the unattenuated radiation transmitted through a particular cross section of the body;
   displacement means for relatively displacing said detectors and said fan beam along the axis of said body to irradiate and to measure the unattenuated transmitted radiation through successive cross sectional areas of the body; and
   display means responsive to said detector electrical signals to display a two dimensional representation of the characteristic radiation absorption of the scanned cross-sectional areas of the body.

2. The apparatus of claim 1 wherein said source means generates X-rays.

3. The apparatus of claim 1 wherein said collimating means includes an energy opaque plate having an energy transparent arc-shaped slit for collimating said penetrating radiation to form said arc-shaped fan beam.

4. The apparatus of claim 3 wherein said arc-shaped slit is a circular arc of substantially $2\pi/3$ radians.

5. The apparatus of claim 1 wherein said means for rotating the detectors includes a disc that supports said detectors in a circular array.

6. The apparatus of claim 5 wherein the radiation sensitivity of each of said detectors is stable within a time interval defined by the time for a single rotation of said disc.

7. The apparatus of claim 1 wherein each detector includes:
  means for converting incident radiation to light energy, but
  photodetecting means responsive to said light energy to generate an electrical signal with an amplitude that is a function of the intensity of the incident radiation.

8. The apparatus of claim 1 wherein said displacement means includes means for moving said fan beam and said detectors while said body remains stationary.

9. The apparatus of claim 1 wherein said detectors are dimensioned to subtend angular widths that are small in comparison to the angular length of said fan beam.

10. The apparatus of claim 1 wherein said collimating means includes a radiation housing means for retaining said source means; and
  an energy opaque plate affixed to the front face of said housing means and having an energy transparent arc-shaped slit for collimating said penetrating radiation to form said arc-shaped fan beam.

11. The apparatus of claim 10 wherein said energy opaque plate defines a collimation face and said displacement means includes means for continuously moving said radiation housing means and said rotating means along the axis of said body in a direction perpendicular to an axis of rotation of said detectors, said axis of rotation aligned perpendicular to said collimation face.

12. The apparatus of claim 11 wherein said displacement means further includes means for continuously moving said energy opaque plate in a direction opposite to the direction of movement of said housing means to maintain the arc-shaped slit of said plate in a particular position for at least one revolution of said rotating means; and
  means for incrementally moving said plate a particular distance in the direction of movement of said housing means after said at least one revolution of said rotating means to define a next successive position for said arc-shaped slit.

13. The apparatus of claim 1 wherein said display means includes an imaging means for receiving electrical signals and displaying a corresponding two dimensional image; and
  a signal transfer means for transferring the electrical signals from the rotating detectors to the imaging means.

14. The apparatus of claim 13 wherein said signal transfer means includes:
  optical emitter means moving synchronously with said rotating means for receiving the electrical signals of said detectors and converting the electrical signals to corresponding light signals; and
  optical receiver means stationary with respect to said optical emitter means for receiving said light signals and generating corresponding electrical signals for said imaging means.

15. The apparatus of claim 13 wherein said imaging means is a cathode ray tube.

16. The apparatus of claim 14 wherein said optical emitter means includes an array of light emitting diodes.

17. The apparatus of claim 14 wherein said optical receiver means includes photodetectors.

18. The apparatus of claim 14 including multiplexer means for receiving electrical signals from groups of three detectors, the detectors in each group being spaced 120° apart, said multiplexer means having means for applying the signals associated with each detector group to a corresponding optical emitter means.

19. The apparatus of claim 18 wherein said multiplexer means includes an adder.

20. Radiant energy imaging apparatus comprising:
  source means for generating an arc-shaped beam of penetrating radiant energy;
  an array of radiant energy detectors defining a curve for receiving radiant energy from said arc-shaped beam;
  means for rotating said array of detectors to provide for each detector an image signal representative of the radiant energy response of an arc-shaped area of a medium that is traversed by said beam along a path to said detectors;
  means for relatively displacing said medium and an assembly including said source and said detectors to establish relative translating motion so that the image signals of said array of detectors are representative of the radiant energy response of a series of parallel arc-shaped areas of the medium; and
  display means responsive to said image signals for producing a two-dimensional image representative of said radiant energy response.

21. The radiant energy imaging apparatus of claim 20 wherein said radiant energy includes X-rays.

22. The radiant energy imaging apparatus of claim 21 wherein each of said detectors includes:
  means for converting incident X-ray energy into light energy; and
  photodetecting means responsive to said light energy for providing an electrical image signal that is amplitude modulated in proportion to some function of the instantaneous X-ray intensity incident upon said detector.

23. The radiant energy imaging apparatus of claim 22 wherein:
  said means for converting X-ray energy to light energy is a crystal from the group consisting of sodium iodide, cesium iodide, and bismuth germanate; and
  said photodetecting means includes a photomultiplier tube connected to the crystal.

24. The radiant energy imaging apparatus of claim 22 wherein:
  said means for converting X-ray energy to light energy is a crystal from the group consisting of sodium iodide, cesium iodide, and bismuth germanate; and
  said photodetecting means includes a solid state detector connected to the crystal.

25. The radiant energy imaging apparatus of claim 21 wherein each of said detectors includes solid state means for converting incident X-ray energy to an electrical signal with an amplitude that is a function of the instantaneous X-ray intensity on said detector.

26. The radiant energy imaging apparatus of claim 20 wherein said source of the arc-shaped beam comprises:
  means for generating radiant energy; and means for collimating said radiant energy into an arc-shaped beam of radiant energy.

27. The radiant energy imaging apparatus of claim 26 wherein said radiant energy includes X-rays.

28. The radiant energy imaging apparatus of claim 26, wherein said collimating means includes a plate of radiant energy opaque material formed with a slit of energy transparent material in the shape of the arc of a circle.

29. The radiant imaging apparatus of claim 28 wherein said slit of radiant energy transparent material is in the shape of an arc of substantially $2\pi/3$ radians.

30. The radiant imaging apparatus of claim 29 wherein said radiant energy includes X-rays.

31. The radiant energy imaging apparatus of claim 20 wherein said means for rotating includes a rotating disc for supporting said detectors.

32. The radiant energy imaging apparatus of claim 31, wherein said disc supports said detectors in a circular array.

33. The radiant energy imaging apparatus of claim 20 wherein said means for relatively displacing includes means for moving the assembly including the source and the detectors while the medium remains stationary.

34. The radiant energy imaging apparatus of claim 20 wherein said detectors are dimensioned to subtend angular widths that are small in comparison to the angular length of said arc-shaped bean of radiant energy.

35. The radiant energy imaging apparatus of claim 20 wherein said means for rotating the detectors rotates to scan each detector across said arc-shaped beam to provide an independent measurement for each detector of the radiation response of an arc-shaped area of said medium, and said assembly is translated a particular distance during each rotation of the detector rotating means to irradiate a next successive arc-shaped area of said medium.

* * * * *